United States Patent [19]
Kim

[11] Patent Number: 5,967,776
[45] Date of Patent: Oct. 19, 1999

[54] AUXILIARY TOOL FOR OCCLUDING APPARATUS AND METHOD OF MOUNTING DENTIFORM MODEL ON OCCLUDING APPARATUS

[76] Inventor: Han-Joon Kim, c/o Kim Orthodontic Clinic, Pain Kurakuen 2F, 3-3, Ishibane-cho, Nishinomiya-shi, Hyogo-ken 662-0074, Japan

[21] Appl. No.: 09/134,996

[22] Filed: Aug. 17, 1998

[51] Int. Cl.[6] ................................................. A61C 11/00
[52] U.S. Cl. ................................................. 433/60; 433/54
[58] Field of Search .................................. 433/60, 63, 65, 433/54, 34, 37, 48, 67

[56] References Cited

U.S. PATENT DOCUMENTS

| | | | |
|---|---|---|---|
| 2,697,279 | 12/1954 | Clawson | 433/60 |
| 4,030,197 | 6/1977 | Linck, II et al. | 433/60 |
| 4,163,319 | 8/1979 | Ouaknine | 433/60 |
| 4,207,677 | 6/1980 | Lampert | 433/60 |
| 4,744,751 | 5/1988 | Finkelstein et al. | 433/60 |
| 5,221,203 | 6/1993 | Callne | 433/60 |
| 5,352,117 | 10/1994 | Silva | 433/60 |
| 5,605,456 | 2/1997 | Young | 433/60 |
| 5,622,497 | 4/1997 | Cho | 433/60 |
| 5,749,725 | 5/1998 | Chinlund | 433/60 |

*Primary Examiner*—Gene Mancene
*Assistant Examiner*—Pedro Philogene
*Attorney, Agent, or Firm*—Rabin & Champagne P.C.

[57] ABSTRACT

An occluded state and an opened state are reproduced on an occluding apparatus by a pair of upper and lower dentiform models using a bite at the time of occlusion and a bite at the time of opening which are extracted from a patient. For the reproduction, a D plate (Dual Mounting Plate) 9 is used. When the D plate 9 is used, it is possible to produce a C block which is integrated with an upper jaw teeth mode 4 by gypsum and an S1 block (or an S2 block) for a spacer which is mounted between the C block and an upper mounting plate 11 (12). The occluded state and the opened state can be reproduced using the dentiform models by replacing the S1 block and the S2 block with each other.

13 Claims, 8 Drawing Sheets

AT THE TIME OF OPENING

PRIOR ART

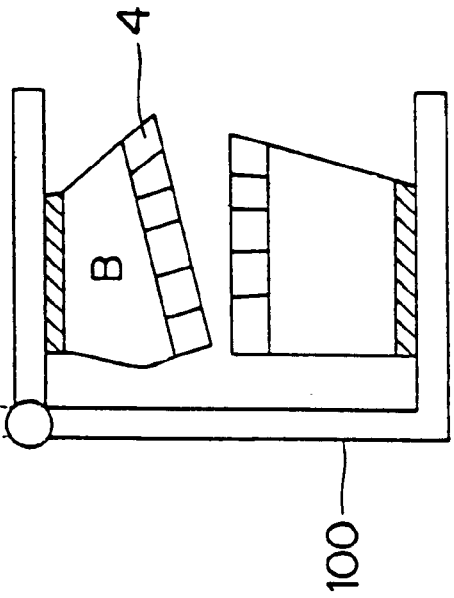
FIG. 3 (A) AT THE TIME OF OCCLUSION
PRIOR ART
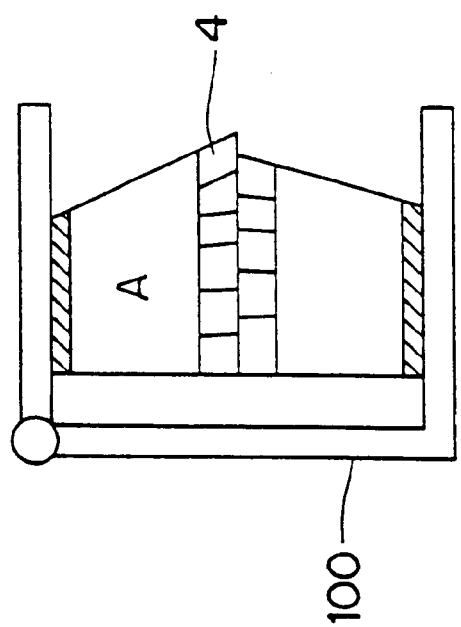
FIG. 3 (B) AT THE TIME OF OPENING
PRIOR ART

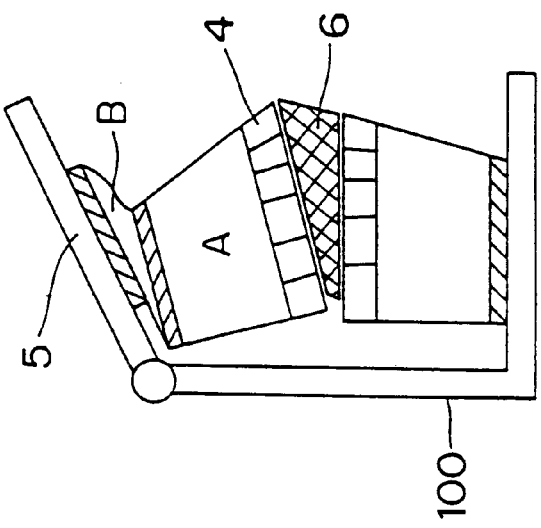
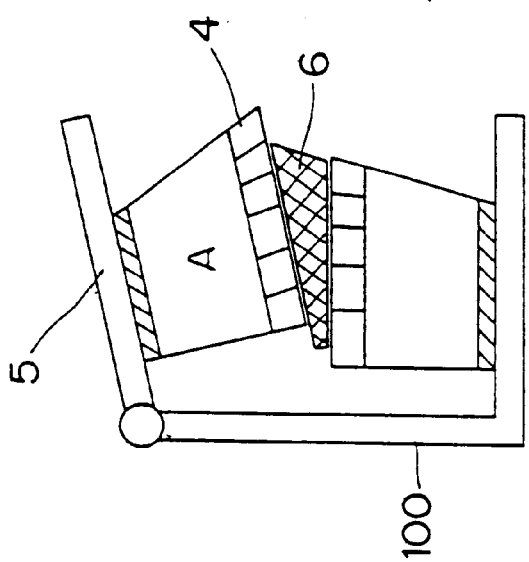
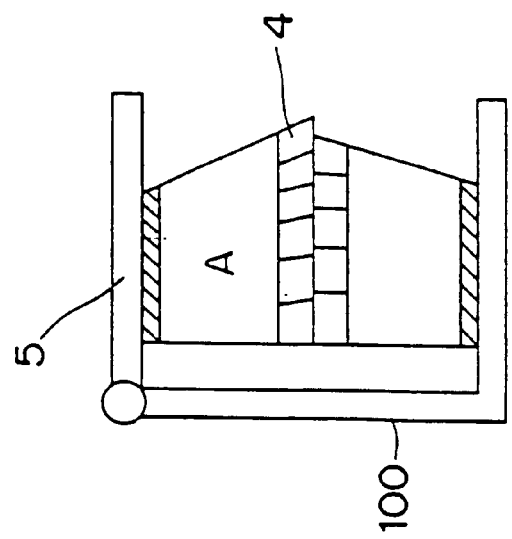
FIG. 4(A) AT THE TIME OF OCCLUSION  PRIOR ART
FIG. 4(B) AT THE TIME OF OPENING  PRIOR ART
FIG. 4(C) AT THE TIME OF OPENING  PRIOR ART

AT THE TIME OF OPENING

AT THE TIME OF OCCLUSION

AUXILIARY TOOL FOR OCCLUDING APPARATUS AND METHOD OF MOUNTING DENTIFORM MODEL ON OCCLUDING APPARATUS

This application is based on an application No. 9-35073 filed in Japan, the content of which is incorporated hereinto by reference.

BACKGROUND OF THE INVENTION

1. Field of the Invention

The present invention relates to a method of an auxiliary tool used when a dentiform model is mounted on an occluding apparatus and a method of mounting the dentiform model on the occluding apparatus. Particularly, it relates to an auxiliary tool for an occluding apparatus which is suitable for production of a tooth positioner used in the final stage, for example, of orthodontic treatment and a method of mounting a dentiform model.

2. Prior Art

In clinical orthodontics, a tool referred to as a tooth positioner has been known as an apparatus used in the final stage of orthodontic treatment for attaining closer occlusion and slightly moving the teeth of a patient in cases such as a case where a relapse occurs in a short time after the orthodontic treatment. The tooth positioner is produced on the basis of a set-up model of the patient, which is made by separating teeth of a dentiform model made on the basis of an impression of the upper and lower Jaws of the patient as required and rearranging the separated teeth in an ideal set of teeth and in an ideal occluded state on the model.

The tooth positioner has a structure similar to a mouse piece (used in sports such as boxing), and is made of a material having elasticity and an original form restoring force, for example, rubber or silicon, so that an ideal set of teeth on the set-up model is carved thereon. When the tooth positioner is mounted in the mouth of the patient, the tooth positioner is first deformed by the difference between the actual set of teeth of the patient and the set of teeth on the set-up model which is carved in the tooth positioner. Thereafter, a continuous weak force is applied to the set of teeth during a mounting period by the original form restoring force of the tooth positioner, to finally move the teeth of the patient to an ideal position indicated by the set-up model. The use of the apparatus eliminates the necessity of using a complicated apparatus in the final stage of the orthodontic treatment, or makes it possible to shorten a period during which a complicated apparatus is mounted. In recent years, such usefulness has been reconsidered, so that the tooth positioner tends to be relatively often used.

FIG. 1 is a perspective view showing an example of a tooth positioner, and FIG. 2 illustrates the tooth positioner in a state where it is mounted in the mouth of a patient. An ideal set of teeth 2 on a set-up model is carved, as described above, in a tooth positioner 1. The set of teeth of the upper jaw 2 and a set of teeth of the lower jaw (not shown) are generally carved.

When the tooth positioner 1 is mounted in the mouth, the set of teeth 2 carved in the tooth positioner 1 and actual sets of teeth $T_U$ and $T_D$ of a patient are engaged with each other. However, after the tooth positioner 1 is deformed by the difference therebetween. A continuous weak force is applied to the actual sets of teeth $T_U$ and $T_D$ by an original form restoring force. The applied force is illustrated by + and − in FIG. 2.

In the tooth positioner 1, however, an occluded surface between the set of teeth of the upper Jaw $T_U$ and the set of teeth of the lower jaw $T_D$ (a surface where the upper and lower teeth are occluded) is covered with its material, so that the tooth positioner 1 is interposed between the upper and lower sets of teeth $T_U$ and $T_D$ (an area indicated by 3 in FIG. 2). That is, when the tooth positioner 1 is mounted, the upper jaw and the lower jaw are opened. Actually, the upper jaw is fixed to the head, so that the lower jaw is opened downward toward the back using the jaw joint as its axis.

The set-up model for the patient is made in a state where the respective sets of teeth of the upper jaw and the lower jaw are occluded. The reason for this is that the occluded surface and the size and the shape of the teeth differ from patient to patient, so that the arrangement of the teeth in an ideal occluded state cannot be presumed.

On the other hand, the tooth positioner is produced in a state where the set-up model made in the occluded state is opened by a suitable amount, that is, the upper and lower jaws are opened by the thickness of the tooth positioner to be interposed between the respective sets of teeth of the upper jaw and the lower jaw.

Consequently, the setting of a state where the jaws are moved when they are opened must conform to the anatomical and physiological functions in the jaw joints of the patient. Otherwise the respective sets of teeth of the upper and lower jaws would not be actually satisfactorily occluded, or would be occluded in an erroneous relationship between the upper and lower jaws after detaching the tooth positioner even if they are respectively regularly corrected by using the tooth positioner. As a result, the sets of teeth may be shifted immediately after the orthodontic treatment, and an excessive burden may be imposed on the jaw joints which correct the shift in the relationship between the upper and lower jaws for each bite. In either case, the mounting itself of a tool produced by unsuitably setting the relationship between the upper and lower jaws distorts the position of the lower jaw, thereby imposing a burden on the jaw joint.

In order to remove such harmful effects, an occluding apparatus and a side X-ray have been conventionally used in setting the amount of opening between the upper and lower jaws.

The occluding apparatus is an apparatus for connecting the upper jaw, the lower jaw and the dentiform model to one another, to reproduce the motion of the jaw joints of a human being. However, the apparatus is an apparatus for confirming a state where the sets of teeth are occluded, and the motion of the jaw joints is only reproduction of a certain degree of average motion. That is, the occluding apparatus has not been able to correctly reproduce the motion of the jaw joints for each patient.

Consequently, it is impossible to faithfully reproduce a state where the upper and lower jaws of each patient are opened by merely using the occluding apparatus.

A method using the side X-ray is a method of respectively tracing the set of teeth of the upper jaw and the set of teeth of the lower jaw on an X-ray of the face taken from just beside the face, opening the set of teeth of the lower jaw using the jaw joint as its axis, referring to the distance between the sets of teeth of the upper and lower jaws (a clearance) which occurs at that time, and setting the motion of the jaw joint. However, the method has the disadvantage in that it is almost impossible to clearly take an X-ray of the left and right jaw joints with they being exactly overlapped with each other. Even if the X-ray can be taken, the accuracy of the X-ray is not sufficient in that the motion in a three-dimensional manner of a state where the upper and lower jaws of the patient are opened is represented in a two-dimensional manner by the X-ray taken from just beside the face.

When the foregoing is considered, it will be said that a method of recording a state where the patient actually bites and a state where the jaws are opened by the thickness of the tooth positioner and reproducing the two types of states on the occluding apparatus is most accurate in order to know the relationship between the upper and lower jaws. The reason for this is that it is not so difficult for a skilled dentist to set the correct occlusion and opening positions of the patient in the mouth of the patient and make a recording of the relationship between the upper and lower jaws (hereinafter referred to as "bite"). In order to take a bite, a material which is mainly composed of silicon and is superior in operability and reproducibility is easily available.

However, it was infeasible from the following reasons to reproduce the two types of relationships between the upper and lower jaws at the time of occlusion and at the time of opening an occluding apparatus using two types of bites extracted from the patient.

In mounting the dentiform model on the occluding apparatus, there are currently a method of directly fastening upper and lower jaw teeth models, respectively, to portions, corresponding to the upper jaw and the lower jaw, of the occluding apparatus by gypsum and a method of fixing a dentiform model to the occluding apparatus using a magnet or a screw such that the dentiform model is detachable from the occluding apparatus as required. In the latter method, a mounting plate of a magnet type or a screw type or a so-called split cast is generally used. In producing the tooth positioner, the latter method in which the dentiform model is detachable from the occluding apparatus is suitable in terms of technical operations.

Consider a case where the relationships between the upper and lower jaws in two states, that is, a state where the respective sets of teeth of the upper and lower jaws are occluded and a state where they are opened by the thickness of the tooth positioner are reproduced on the occluding apparatus utilizing the two types of bites extracted in the mouth of the patient. In reproducing the two types of states on the occluding apparatus, it is considered that the upper jaw teeth model is mounted in the following two types of methods without changing the position where the lower jaw teeth model is mounted.

(1) Only two upper jaw teeth models which are the same are prepared, to respectively be mounted, using the bite extracted in the occluded state and the bite extracted in the opened state, the two states on an upper jaw portion of the occluding apparatus.

In this case, two types of blocks A and B for the upper jaw, including an upper jaw teeth model 4, are formed, as shown in FIGS. 3 (A) and 3 (B) (the A block reproduces the occluded state, and the B block reproduces the opened state). Accordingly, the two types of relationships between the upper and lower jaws can be reproduced by replacing the two blocks A and B with each other on an occluding apparatus 100.

Even if teeth of the dentiform model in the occluded state shown in FIG. 3 (A) are separated, and the separated teeth are newly rearranged, to make a set-up model, however, the set-up model cannot be brought into the state shown in FIG. 3 (B), that is, the opened state. Conversely, a set-up model cannot be produced from the dentiform model in the opened state shown in FIG. 3 (B). The reason for this is that the form of the teeth differs from patient to patient, so that the arrangement of the teeth in the occluded state cannot be presumed from the opened state, and the set-up model cannot be made from the dentiform model which is not in the occluded state.

(2) As another method, consider a method of reproducing the two types of relationships between the upper and lower jaws not using the two upper jaw teeth models but using a pair of upper and lower jaw teeth models. In this case, a state at the time of occlusion is obtained, in the same manner as that shown in FIG. 3 (A), as shown in FIG. 4 (A). However, an attempt to reproduce a state at the time of opening brings about the necessity of opening an upper jaw portion 5 of the occluding apparatus 100 itself, as shown in FIG. 4 (B).

The occluding apparatus 100 reproduces the motion of the jaw joints of a human being in approximate or average fashion, and does not faithfully reproduce the motion of the jaw joints of each patient, as described above. Even if an attempt to finely adjust the position where the A block is mounted with a bite 6 interposed between the lower jaw teeth model and the upper jaw teeth model is made in the state shown in FIG. 4 (B), the upper jaw teeth model 4 cannot be so adjusted as to fit the bite 6.

An attempt to make the adjustment brings about the necessity of further fastening the B block for correction on the A block.

In this case, even if the relationship between the upper and lower jaws at the time of opening can be reproduced, the B block for correction is fastened to the A block. In the A block A plus B block, therefore, the occluded state shown in FIG. 4 (A) cannot be reproduced even if the upper jaw portion 5 of the occluding apparatus 100 is lowered (closed).

As apparent from the foregoing consideration, in the method currently used, it is impossible to reproduce the two types of relationships between the upper and lower jaws which are required to produce the tooth positioner on the occluding apparatus.

SUMMARY OF THE INVENTION

An object of the present invention is to provide an auxiliary tool for reproducing on an occluding apparatus two types of relationships between the upper and lower jaws at the time of occlusion and at the time of opening which are required to produce a tooth positioner using two types of bites extracted in the mouth of a patient.

Another object of the present invention is to provide a method of using an occluding apparatus on which it is possible to reproduce a plurality of types of relationships between the upper and lower jaws of a patient utilizing bites, in different relationships between the upper and lower jaws, extracted in the mouth of the patient and an auxiliary tool required therefor.

Still another object of the present invention is to provide a method of mounting on an occluding apparatus a dentiform model capable of reproducing a plurality of types of relationships between the upper and lower jaws of a patient on the occluding apparatus.

In the auxiliary tool according to the present invention, the other dentiform model can be mounted on the occluding apparatus with the spacer member having a predetermined thickness interposed between the dentiform model and the occluding apparatus. The spacer member is attachable and detachable to and from the main plate fixed to the dentiform model. When the spacer member is connected to the main plate, the dentiform model and the spacer member are brought into a predetermined positional relationship by a positioning mechanism. Consequently, the spacer member is always connected to the dentiform model in a predetermined position, thereby eliminating the possibility that the position of the dentiform model is shifted by using the spacer member.

The main plate and the spacer member are connected to each other by a magnetic force or a mechanical connecting mechanism, for example. When the magnetic force is used, the connection between the dentiform model and the spacer member is very simple, and is also easily released. Even in the case of the mechanical connecting mechanism, the dentiform model and the spacer member can be simply attached and detached to and from each other by slightly rotating the dentiform model and the spacer member relative to each other.

By using the auxiliary tool according to the present invention, or in the mounting method according to the present invention, it is possible to reproduce, in the occluding apparatus, the dentiform model of the patient in an occluded state and a predetermined opened state. That is, the dentiform model can be reproduced in a predetermined opened state by using the spacer member at the time of opening. If the spacer member is replaced with the spacer member at the time of occlusion, the dentiform model can be reproduced in an occluded state.

Consequently, it is possible to separate teeth of the dentiform model in the occluded state, newly rearrange the separated teeth to make a set-up model, and reproduce the made set-up model in the predetermined opened state. Accordingly, the tooth positioner can be produced, for example, on the basis of the set-up model reproduced in the opened state.

According to the present invention, the relationship between the upper and lower jaws of a patient can be faithfully reproduced on an occluding apparatus, thereby contributing to the production of a tooth positioner which satisfactorily fits the mouth of the patient.

According to the present invention, it is possible to reproduce a plurality of relationships between the upper and lower jaws of a patient on an occluding apparatus by a pair of upper and lower dentiform models, and provide an auxiliary tool for the occluding apparatus which is useful for clinical orthodontics.

These objects and other objects, features, aspects and advantages of the present invention will become more apparent from the following detailed description of the present invention when taken in conjunction with the accompanying drawings.

BRIEF DESCRIPTION OF THE DRAWINGS

FIGS. 3 (A) and 3 (b) are diagrams showing how only two upper jaw teeth models which are the same are prepared, and are mounted on an occluding apparatus in an occluded state and an opened state.

FIGS. 4 (A), 4 (B) and 4 (C) are diagrams for explaining a method of reproducing two types of relationships between the upper and lower jaws using a pair of upper and lower dentiform models.

DESCRIPTION OF THE PREFERRED EMBODIMENT

Figure 1:
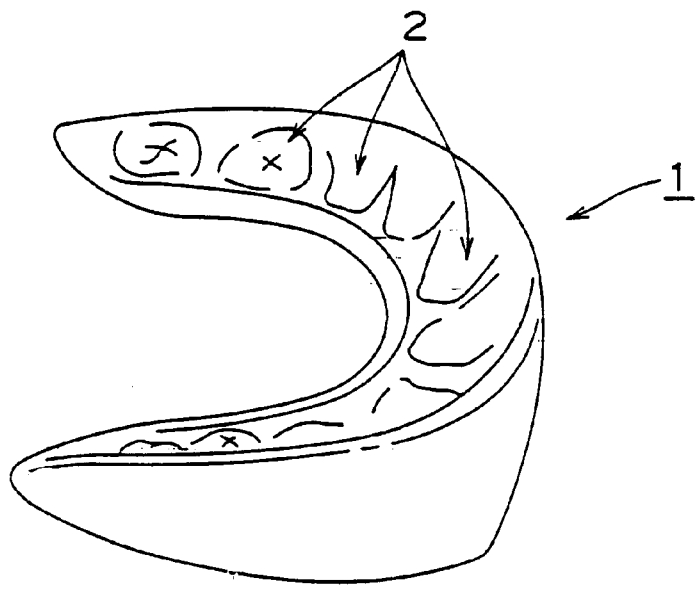
FIG. 1 is a perspective view of an example of a known tooth positioner.
Figure 2:
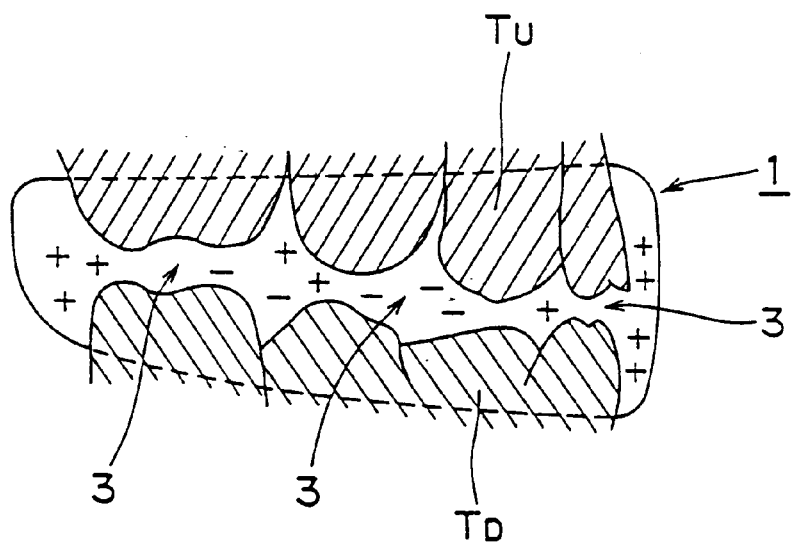
FIG. 2 is an illustration of a state where the tooth positioner is mounted on the mouth of a patient.
Figure 5:
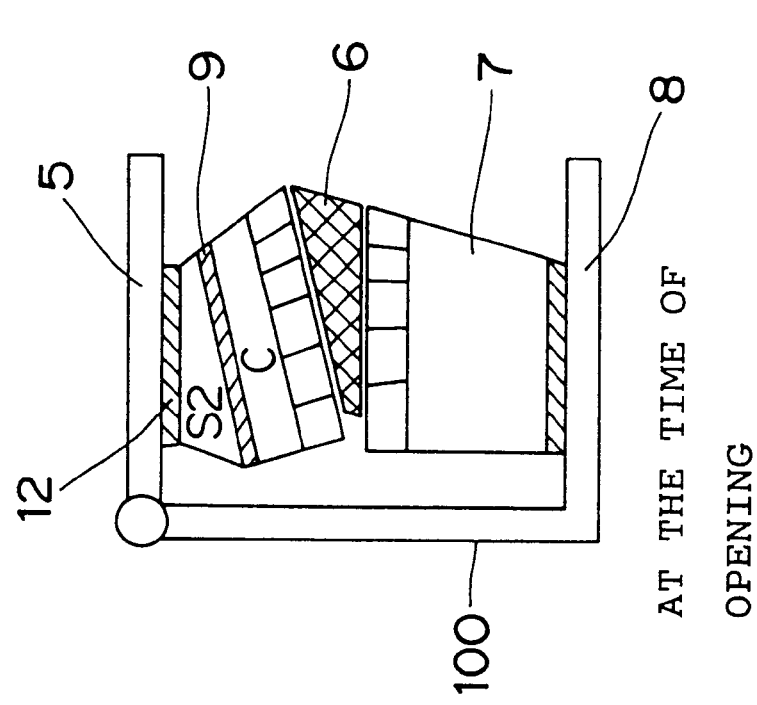
FIGS. 5 (A) and 5 (B) are diagrams for explaining a method of mounting dentiform models on an occluding apparatus using an auxiliary tool according to an embodiment of the present invention.
Figure 5:
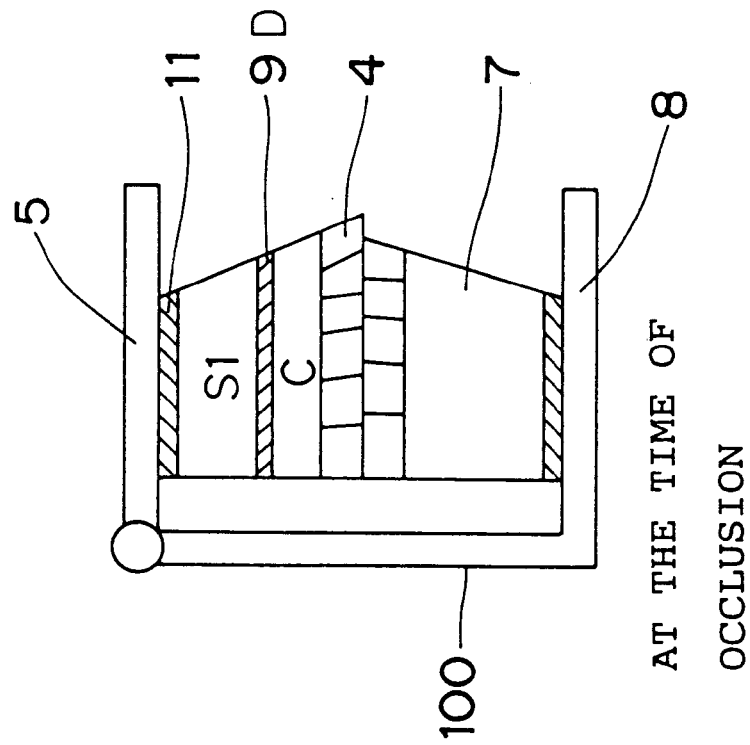

FIGS. 5 (A) and 5 (B) illustrate a method of mounting a dentiform model on an occluding apparatus using an auxiliary tool according to an embodiment of the present invention.

A lower jaw teeth model 7 is first mounted on a lower jaw portion 8 of an occluding apparatus 100. After the mounting, the position where the lower jaw teeth model 7 is mounted shall not be changed, and an upper jaw teeth model 4 shall be mounted on the basis of the lower jaw teeth model 7.

In mounting the upper jaw teeth model 4, a D plate 9 (Dual Mounting Plate: the specific structure of the D plate will be described later) is first mounted on the upper jaw teeth model 4 by gypsum, for example. A block obtained by integrating the upper jaw teeth model 4 and the D plate 9 by the gypsum shall be referred to as a C block.

The C block is mounted on the occluding apparatus 100 using a bite at the time of occlusion (not shown) which is extracted, when the teeth of a patient are occluded, in the mouth of the patient (reproduction at the time of occlusion can be also performed without the bite). The C block is mounted by mounting a mounting plate 11 on an upper jaw portion 5 of the occluding apparatus 100, positioning the C block in a predetermined position with respect to the lower jaw teeth model 7 using the bite at the time of occlusion, and filling a portion between the positioned C block and the mounting plate 11 and more specifically, a portion between the D plate 19 and the mounting plate 11 with gypsum. When the gypsum is set, the mounting plate 11 is integrated with the gypsum. A block obtained by the integration shall be referred to as an S1 block. It can be said that the S1 block functions as a spacer mounted between the D plate 9 and the upper jaw portion 5 of the occluding apparatus 100 when the lower jaw teeth model 7 is in an occluded state.

When the D plate is used, the S1 block above the D plate can be detached from the D plate.

The C block and the S1 block are then detached from the occluding apparatus 100 in a state where the relationship between the upper and lower jaws at the time of occlusion which is formed in the above-mentioned manner is reproduced (a state shown in FIG. 5 (A)). The C block including the D plate 9 can be detached from the S1 block, as described above. Further, the S1 block including the mounting plate 11 is attachable and detachable to and from the upper jaw portion 5 of the occluding apparatus 100.

The reproduction at the time of opening will be described. The C block is mounted on the same occluding apparatus 100 using a bite at the time of opening 6 which is extracted, when the mouth of the patient is opened. Specifically, a mounting plate 12 (the mounting plate 12 is a plate other than the mounting plate 11 used in FIG. 5 (A) (which is the same in type)) is mounted on the upper jaw portion 5 of the occluding apparatus 100, the upper jaw teeth model 4, that is, the C block is placed in a predetermined position with respect to the lower Jaw teeth model 7 using the bite at the time of opening 6, and gypsum is piled between the D plate 9 in the C block and the mounting plate 12, to make an S2 block. Although the S2 block is integrated with the mounting plate 12, it is attachable and detachable to and from the D plate 9. It can be said that the S2 block functions as a spacer mounted between the D plate 9 and the upper jaw portion 5 of the occluding apparatus 100 when the lower jaw teeth model 7 is in an opened state.

As described in the foregoing, the C block, the S1 block and the S2 block are prepared. The C block is used for two types of mounting at the time of occlusion and at the time of opening, and is identical. By replacing the S1 block and the S2 block with each other, therefore, two types of relationships between the upper and lower jaws can be reproduced on the same occluding apparatus 100 or the occluding apparatuses 100 in the same state (setting) and by the pair of upper and lower jaw teeth models 4 and 7.

In the case of setup, therefore, work is performed by combining the C block with the S1 block and mounting their combination on the occluding apparatus 100, to reproduce the relationship between the upper and lower jaws at the time of occlusion. After completion of the setup, it is possible to produce a tooth positioner by combining the C block set up with the S2 block and mounting their combination on the occluding apparatus 100 this time.

Description is now made of the D plate.

Figure 6:
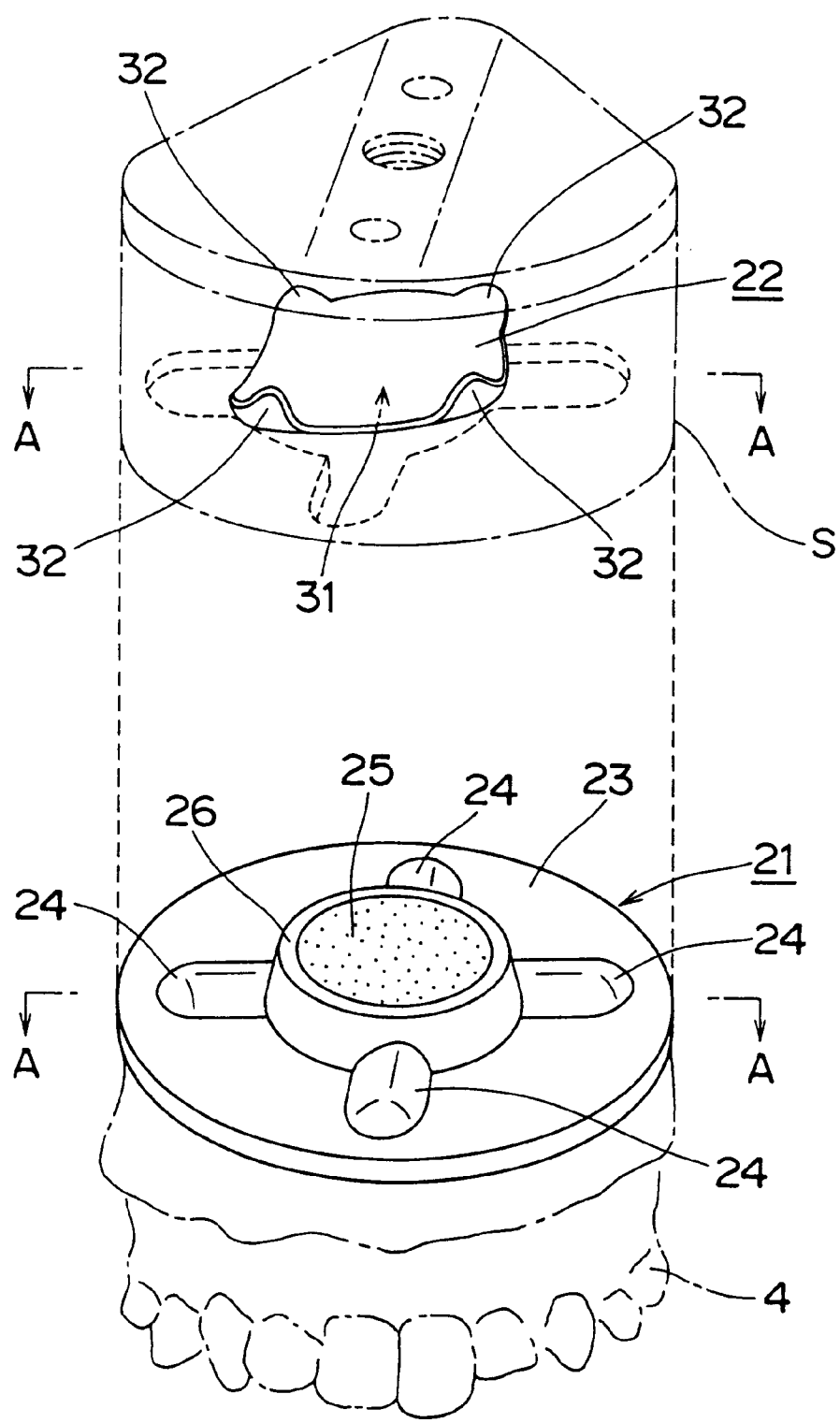
FIG. 6 is a perspective view showing an example of a D plate according to an embodiment of the present invention.

FIG. 6 is a perspective view showing an example of the D plate. For reference, the upper jaw teeth model 4 and the S block (the S1 block or the S2 block) are indicated by a one-dot and dash line.

The D plate comprises a main plate 21 fastened to the upper jaw teeth model 4 and an auxiliary plate 22 fastened to the S block. The main plate 21 comprises a thin plate in a disk shape which is formed of resin, for example, and the upper jaw teeth model 4 is fastened to the lower surface thereof. Positioning projections 24 are formed on an upper surface 23 of the main plate 21. A magnetic member 25 is disposed at an approximately central part, for example, of the upper surface 23. In the present embodiment, an enclosure 26 which encloses the magnetic member 25 is formed on the upper surface 23, and the projections 24 extend in four directions from the enclosure 26.

The projection 24 is a projection for positioning. An outer surface of the projection 24 is brought into a smooth convex surface in order to prevent gypsum piled on the upper surface 23 of the main plate 21 (gypsum forming the S block) from coming off the projection 24. Further, the upper surface 23 of the main plate 21 is finished to a smooth surface in order to prevent, when gypsum is piled thereon to form the S block, the gypsum from coming off the upper surface 23.

The auxiliary plate 22 comprises an abutted surface 31 and four small embedded members 32 projecting in four directions from the abutted surface 31, and is formed of a metal plate (e.g., an iron plate or a stainless plate) such that it is attracted by the magnetic member 25. The auxiliary plate 22 which becomes a part of the S block upon adhering to the S block enters a state where the lower surface of the abutted surface 31 is so exposed as to be abutted against the upper surfaces of the magnetic member 25 and the enclosure 26, while the embedded members 32 are embedded in the gypsum on the D plate.

Figure 7:
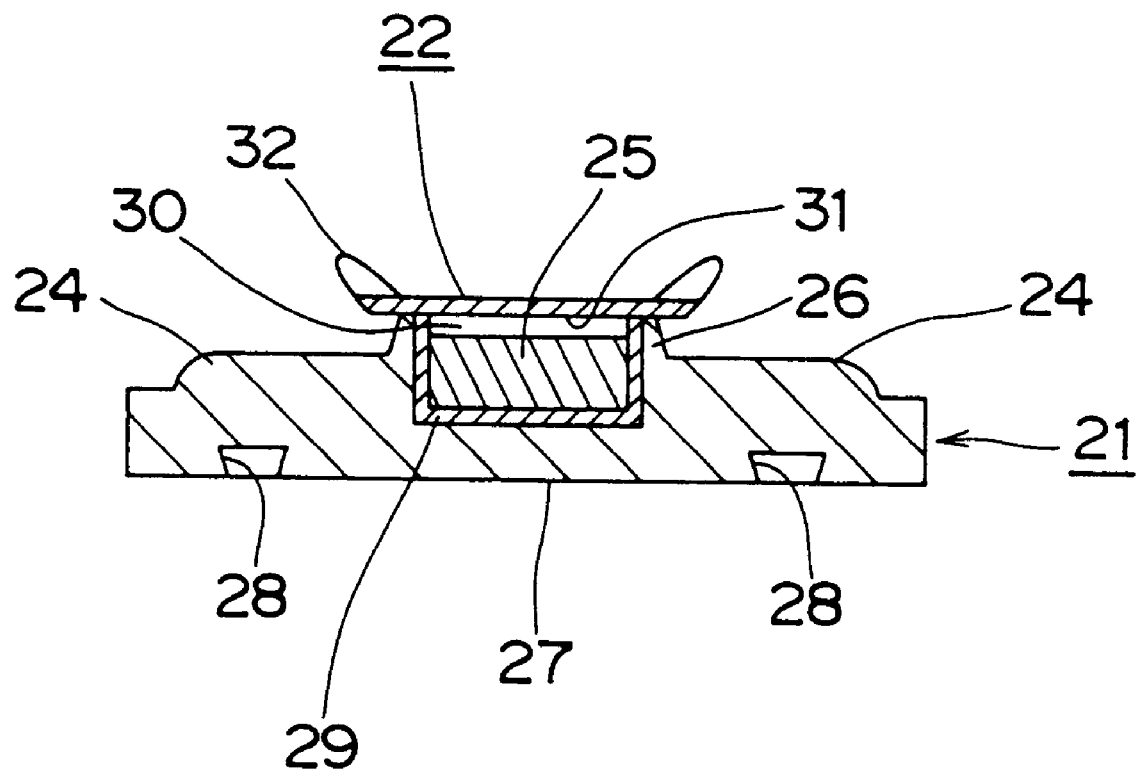
FIG. 7 is a cross-sectional view taken along a line A—A shown in FIG. 6.

A cross-sectional view of the main plate 21 and the auxiliary plate 22 along a line A—A shown in FIG. 6 is illustrated in FIG. 7. FIG. 7 illustrates a state where the auxiliary plate 22 is abutted against the main plate 21. In fastening the upper jaw teeth model by gypsum, a plurality of holes 28 are formed on a lower surface 27 of the main plate 21 such that the gypsum firmly adheres to the main plate 21. The holes 28 shall be preferably undercut holes. Instead of forming the holes 28, the lower surface 27 may be roughened, and projections to which gypsum easily adheres may be formed on the lower surface 27.

A metal member 29 made of iron, for example, in a cylindrical plate shape is arranged in the enclosure 26 along an inner peripheral surface of the enclosure 26, and the magnetic member 25 is set in the metal member 29. The metal member 29 and the magnetic member 25 are bonded to each other with adhesives, for example, and the metal member 29 is bonded to the main plate 21.

The auxiliary plate 22 is formed in such sizes that the abutted surface 31 covers at least the periphery of the magnetic member 25, that is, an upper edge of the metal member 29. Even if a clearance 30 exists on the upper surface of the magnetic member 25, therefore, it is possible to prevent, when gypsum is piled to form the S block, the gypsum from entering the clearance 30.

The main plate 21 may be formed of ceramics or a metal in addition to resin.

Figure 8:
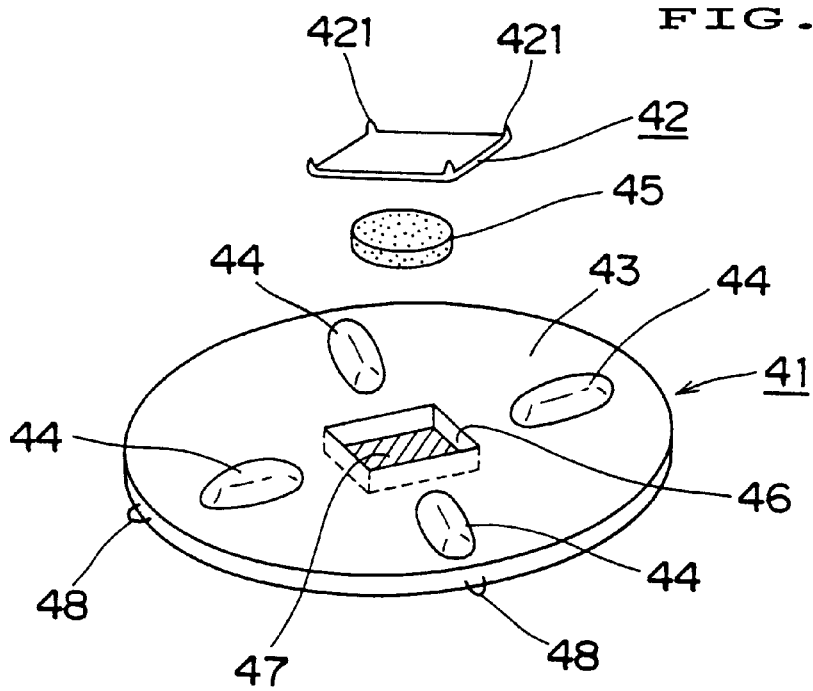
FIGS. 8 (A), 8 (B) and 8 (C) are diagrams showing an example of the structure of a D plate according to another embodiment of the present invention.
Figure 8:
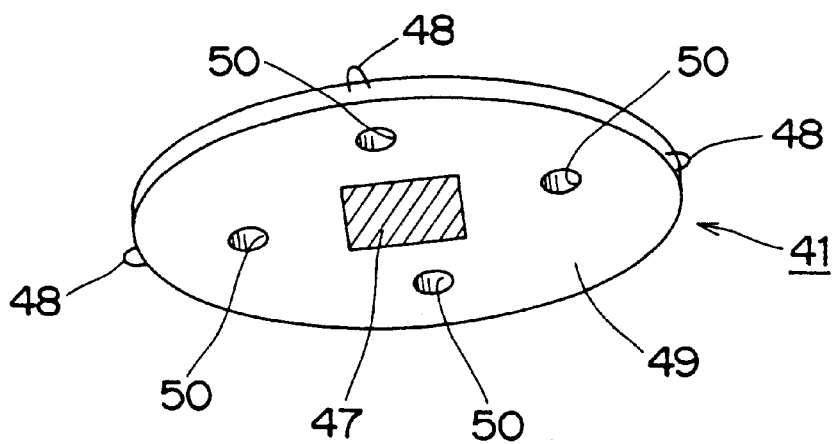
Figure 8:
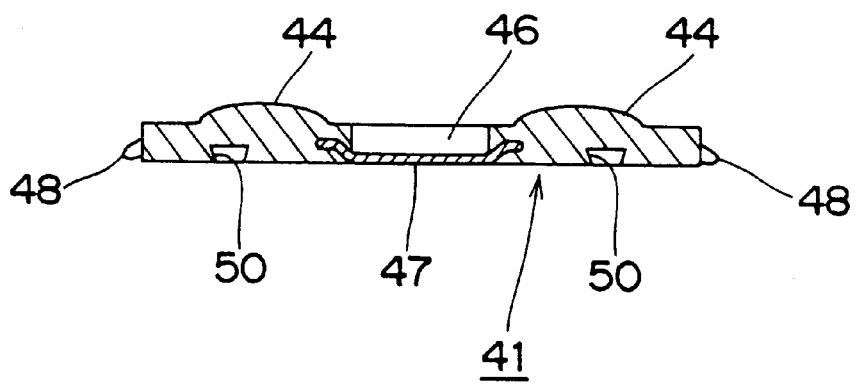

FIGS. 8 (A), (B) and (C) illustrate examples of the structure of a D plate according to another embodiment. The D plate shown in FIG. 8 is made thinner. The merit of making the D plate thin is that the D plate can be satisfactorily used irrespective of the type of occluding apparatuses.

The D plate has a main plate 41, a magnetic member 45 which is detachable from the main plate 41, and a metal plate 42 functioning as an auxiliary plate.

Referring to FIG. 8 (A), the D plate comprises a main plate 41, a plurality of (for example, four) positioning projections 44 which are provided on an upper surface 43 of the main plate 41, and a magnetic member embedding hole 46, formed at an approximately central part of the main plate 41, of a magnetic member 45. A metal plate 47 is arranged on the bottom surface of the embedding hole 46. Further, hooks 48 utilized when a dentiform model is mounted project from an outer peripheral edge of the main plate 41.

Referring to FIGS. 8 (B) and 8 (C), a plurality of undercut holes 50 (four holes in the present embodiment) are preferably formed on a lower surface 49 of the main plate 41, when gypsum adheres on the lower surface 49, such that the gypsum is firmly fixed thereto. The lower surface of the metal plate 47 is flush with the lower surface 49 of the main plate 41.

Also in the main plate 41, it is preferable that the lower surface 49 has a rough finish, while the upper surface 43 has a smooth finish.

The metal plate 42 functioning as an auxiliary plate is formed in such sizes as to completely cover the magnetic member embedding hole 46. When gypsum is piled on the upper surface 43 of the main plate 41, therefore, the gypsum does not enter the hole 46. Engaging members 421 which are embedded in gypsum are formed at four corners of the metal plate 42.

If such a D plate is used, the magnetic member 45 can be detached, and can be repeatedly used. That is, only the main plate 41 and the metal plate 42 may be made disposable, so that the D plate can be constructed at low cost.

Figure 9:
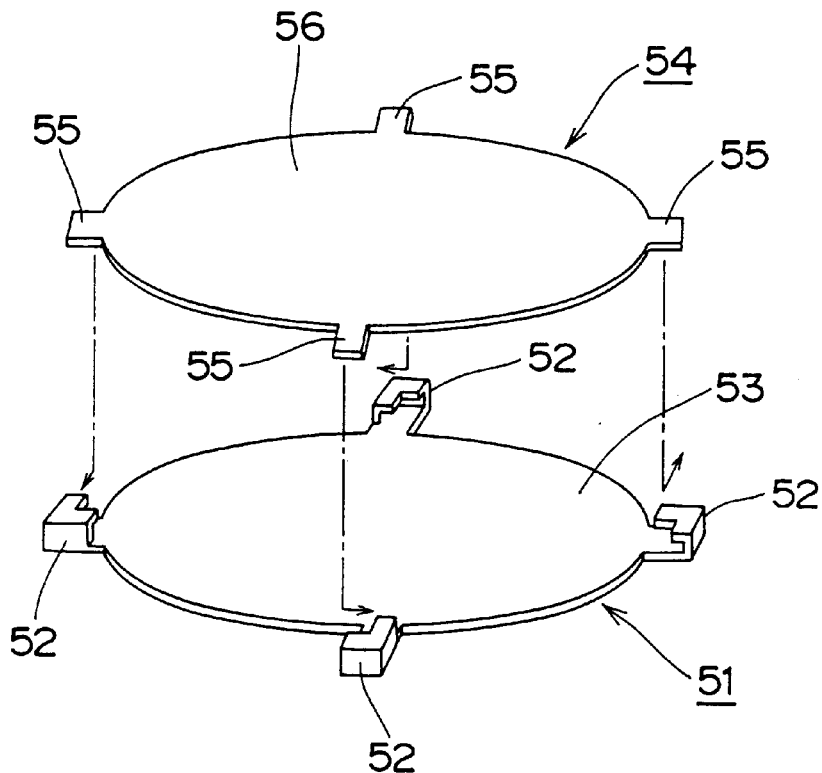
FIG. 9 is a diagram showing an example of the structure of a D plate according to still another embodiment of the present invention.

FIG. 9 illustrates an example of the structure of a D plate according to still another embodiment of the present invention.

The D plate shown in FIG. 9 employs a structure in which a main plate and an auxiliary plate are not attached to each other by a magnetic force but are mechanically fitted to each other.

That is, a main plate 51 is a thin plate in a disk shape which is formed of resin, ceramic, or a metal, for example, and has engaging recesses 52 projecting in four directions from its peripheral edge. No positioning projection is formed, in the present embodiment, on an upper surface 53 of the main plate 51, so that the upper surface 53 is a flat surface.

The auxiliary plate 54 is a thin plate in a disk shape which is formed of resin, ceramic, or a metal, for example, and its plane shape almost coincides with the shape of the main plate 51. Engaging projections 55 are formed in positions, corresponding to the engaging recesses 52 formed at the peripheral edge of the main plate 51, at a peripheral edge of the auxiliary plate 54. The lower surface of the auxiliary plate 54 is a flat surface so as to adhere to the upper surface 53 of the main plate 51.

The main plate 51 and the auxiliary plate 54 are positioned and fixed by abutting the upper surface 53 of the main plate 51 against the lower surface of the auxiliary plate 54 and relatively twisting both their positions in the state so that the engaging projections 55 respectively enter the engaging recesses 52. Since the engaging recesses 52 and the engaging projections 55 respectively project outward from the lower surface of the main plate 51 and the upper surface 56 of the auxiliary plate 54 on which gypsum is to be piled, thereby eliminating possibilities such as the possibility that even if the gypsum is piled, the gypsum is embedded in the engaging recesses 52 and the engaging projections 55.

It is preferable that the lower surface of the main plate 51 and the upper surface 56 of the auxiliary plate 54 are made rough, are provided with holes, and are provided with projections in order to improve the adhesion of the piled gypsum.

Although in the present embodiment, description was made of an example in which four pairs of engaging recesses 52 and engaging projections 55 are provided, the number of pairs may be the number of pairs required to engage the main plate 51 and the auxiliary plate 54 with each other, that is, at least two or more.

Furthermore, the engaging recesses 52 may be in a continuous shape extending along a peripheral edge of the main plate 51.

In short, a fitting pair in such a relationship that the main plate 51 and the auxiliary plate 54 are positioned and fixed may be provided in abutting the auxiliary plate 54 against the main plate 51.

Figure 10:
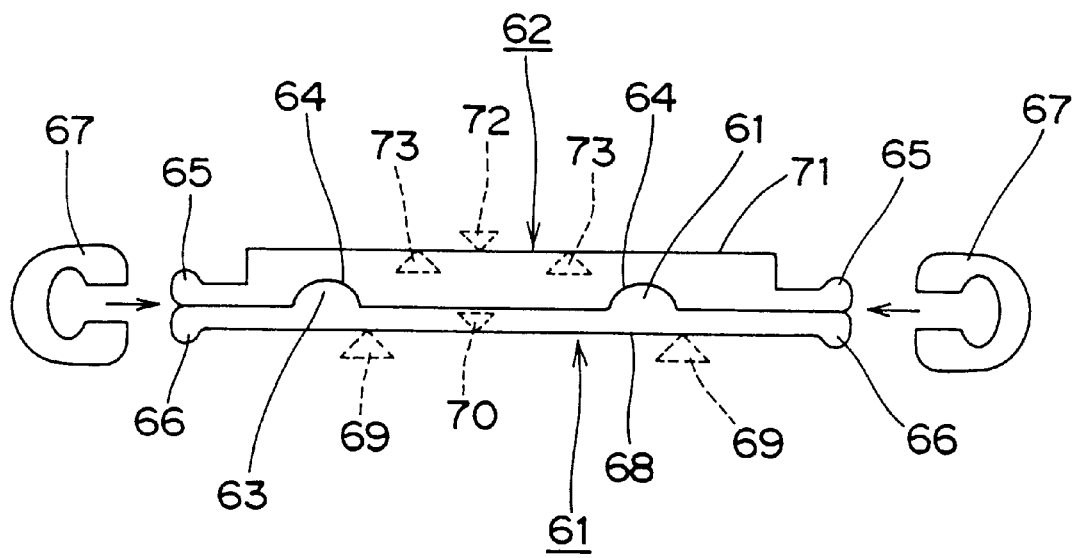
FIG. 10 is a diagram showing an example of the structure of a D plate according to a further embodiment of the present invention.

FIG. 10 shows an example of the structure of a D plate according to a further embodiment of the present invention. The D plate shown in FIG. 10 has a main plate 61 and an auxiliary plate 62 which are formed of resin, ceramics, or a metal, for example, as in FIG. 9. The main plate 61 and the auxiliary plate 62 have approximately equal plane shapes, and the upper surface of the main plate 61 and the lower surface of the auxiliary plate 62 adhere to each other. In order to determine the relative positional relationship between the main plate 61 and the auxiliary plate 62 when both adhere to each other, a projection 63 and a recess 64 are respectively formed on opposite surfaces of one of the plates and the other plate.

Paired projecting members for fixing 65 and 66 are respectively provided at peripheral edges of the main plate 61 and the auxiliary plate 62. The projecting members 65 and 66 are provided in positions which correspond to each other, and are abutted against each other. In the present embodiment, there are provided clips 67 each holding the paired projecting members 65 and 66. The main plate 61 and the auxiliary plate are mounted by respectively holding the paired projecting members 65 and 66 in the clips 67.

Even in the present embodiment, a projection 69 and a hole 70 for firmly fixing piled gypsum may be provided on a lower surface 68 of the main plate 61. Similarly, a projection 72 and a hole 73 for firm adhesion of gypsum may be formed on an upper surface 71 of the auxiliary plate 62.

Although some embodiments of the D plate were specifically described, the D plate according to the present invention is not limited to the above-mentioned embodiments, but is specified by the claims, and can be deformed in various shapes.

A method of using according to the present invention is only limited to the contents of the claims, and is not limited to the contents of the embodiments.

While there has been illustrated and described what is at present considered to be a preferred embodiment of the present invention, it will be understood by those skilled in the art that various changes and modifications may be made, and equivalents may be substituted for elements thereof without departing from the true scope of the invention. It is intended that this invention not be limited to the particular embodiment disclosed as the best mode contemplated for carrying out the invention, but that the invention will include all embodiments falling within the scope of the appended claims.

What is claimed is:

1. An auxiliary tool for mounting which is used when a pair of upper and lower dentiform models is mounted on an occluding apparatus, characterized by comprising:

a main plate fixed to either one of said pair of upper and lower dentiform models; and a sub plate which is attachable and detachable to and from the main plate;

the sub plate being integrated with gypsum by piling the gypsum thereon, to form a spacer member having a predetermined thickness.

2. The auxiliary tool according to claim 1, characterized in that the main plate comprises first positioning means for positioning, and the spacer member comprises second positioning means which is engaged with the first positioning means.

3. The auxiliary tool according to claim 2, characterized in that the first positioning means comprises a projection or recess formed in the main plate, and the second positioning means comprises a recess or projection of the gypsum set along the shape of said projection or recess.

4. The auxiliary tool according to claim 1, characterized in that the main plate or the sub plate comprises a magnetic force generating member, the sub plate or the main plate comprises a member to be attracted which is attracted by a magnetic force, and the main plate and the sub plate are maintained in their connected state by the magnetic force.

5. The auxiliary tool according to claim 4, characterized in that a mounting plate used for attachable and detachable mounting to and from the occluding apparatus is fastened to a surface, on the opposite side of a mounting surface to the main plate, of the spacer member.

6. The auxiliary tool according to claim 5, characterized in that a spacer member in a case where the pair of upper and lower dentiform models is in an occluded state and a spacer member in a case where it is in a predetermined opened state are respectively produced as the spacer member.

7. The auxiliary tool according to claim 3, characterized in that a mounting plate used for attachable and detachable mounting to and from the occluding apparatus is fastened to a surface, on the opposite side of a mounting surface to the main plate, of the spacer member.

8. The auxiliary tool according to claim 7, characterized in that a spacer member in a case where the pair of upper and lower dentiform models is in an occluded state and a spacer member in a case where it is in a predetermined opened state are respectively produced as the spacer member.

9. An auxiliary tool for mounting which is used when a pair of upper and lower dentiform models is mounted on an occluding apparatus, characterized by comprising:

a first plate having a mounting surface to be fixed to either one of said pair of upper and lower dentiform models by gypsum and a first connecting surface on the opposite side thereof;

a second plate having a second connecting surface which is connectable to the first connecting surface and a mounting surface on which gypsum is piled on the opposite side thereof; and positioning means for positioning the relationship of the connection between the first plate and the second plate in a predetermined state.

10. The auxiliary tool according to claim 9, characterized in that the positioning means comprises a fitted portion which is provided in the first plate and a portion to be fitted which is provided in the second plate and is fitted in the fitted portion.

11. A method of mounting a pair of upper and lower dentiform models on an occluding apparatus, characterized by comprising the steps of:

mounting either one of said pair of upper and lower dentiform models on a predetermined mounting portion of the occluding apparatus;

mounting, on a mounting portion, on which the other of said pair of upper and lower dentiform models is to be mounted, of the occluding apparatus, a mounting plate which is detachable from the mounting portion;

fixing an intermediate plate to the other dentiform model by gypsum, and holding the other dentiform model in an occluded state with respect to the one dentiform model mounted on the occluding apparatus; and piling gypsum between the mounting plate mounted on the mounting portion of said occluding apparatus and the intermediate plate fixed to the other dentiform model held in the occluded state, to form a spacer member which is integrally fixed to the mounting plate and is attachable and detachable to and from the intermediate plate.

12. The method according to claim 11, characterized in that the intermediate plate comprises a main plate mounted on the other dentiform model by gypsum and an iron plate attracted toward the main plate by a magnetic force, the iron plate being integrally fixed to gypsum in piling the gypsum thereon to form a spacer member.

13. The method according to claim 9, characterized in that the pair of upper and lower dentiform models is held, using a bite extracted, with respective sets of teeth of the upper and lower jaws in a predetermined opened state, in the mouth of a patient, so as to enter a predetermined opened state reproduced by the bite instead of holding either one of the dentiform models in an occluded state with respect to the other dentiform model.

* * * * *